United States Patent
Okada et al.

(10) Patent No.: US 7,551,768 B2
(45) Date of Patent: Jun. 23, 2009

(54) IMAGE RECOGNITION APPARATUS AND METHOD FOR SURFACE DISCRIMINATION USING REFLECTED LIGHT

(75) Inventors: Yasuichi Okada, Arao (JP); Kimiyuki Yamasaki, Ogoori (JP); Masahiro Kihara, Kurume (JP)

(73) Assignee: Panasonic Corporation, Osaka (JP)

( * ) Notice: Subject to any disclaimer, the term of this patent is extended or adjusted under 35 U.S.C. 154(b) by 771 days.

(21) Appl. No.: 10/753,740

(22) Filed: Jan. 8, 2004

(65) Prior Publication Data
US 2004/0213450 A1   Oct. 28, 2004

(30) Foreign Application Priority Data
Jan. 9, 2003  (JP)  ............... P. 2003-003032
Jan. 9, 2003  (JP)  ............... P. 2003-003033

(51) Int. Cl.
*G06K 9/00*  (2006.01)
*G01B 11/30*  (2006.01)

(52) U.S. Cl. .................... 382/145; 356/602
(58) Field of Classification Search ............ 382/145
See application file for complete search history.

(56) References Cited

U.S. PATENT DOCUMENTS

| | | | |
|---|---|---|---|
| 4,677,473 A | | 6/1987 | Okamoto et al. |
| 4,750,140 A | * | 6/1988 | Asano et al. ............ 382/108 |
| 5,039,868 A | | 8/1991 | Kobayashi et al. |
| 5,064,291 A | * | 11/1991 | Reiser ................. 356/625 |
| 5,462,626 A | * | 10/1995 | Kanayama et al. ....... 156/272.8 |
| 5,764,874 A | * | 6/1998 | White .................. 396/155 |
| 6,040,895 A | | 3/2000 | Haas |
| 6,236,747 B1 | * | 5/2001 | King et al. ............. 382/149 |
| 2001/0013535 A1 | * | 8/2001 | Miyake et al. ........... 228/180.1 |

(Continued)

FOREIGN PATENT DOCUMENTS

JP   02-036893 A   2/1990

(Continued)

OTHER PUBLICATIONS

Machine-generated English translation, JP 2000-028320 A, http://www4.inpit.go.jp/, Jun. 2008.*

(Continued)

*Primary Examiner*—Bhavesh M Mehta
*Assistant Examiner*—David P Rashid
(74) *Attorney, Agent, or Firm*—Pearne & Gordon LLP

(57) ABSTRACT

In an image recognition method, the image of a cream solder 9 printed on a rectangular electrode 16 having a solder leveler formed is picked up and recognized to identify the cream solder 9. An illuminating unit having white light source parts 35W arranged in the radial oblique directions of 45° is used to apply white color illumination lights from a light applying direction in which an angle of $\theta 1$ formed by the light applying direction and a horizontal plane in a vertical plane is 45° or smaller and from a light applying direction in which an angle of $\theta 3$ formed by the light applying direction and the boundary of the electrode 16 in a horizontal plane is 75° or smaller. Thus, regularly reflected lights from a solder leveler forming surface 16*a* with a glossiness are not received by an upper camera to identify a solder surface 9*a* and the solder leveler forming surface 16*a* with good accuracy.

6 Claims, 14 Drawing Sheets

U.S. PATENT DOCUMENTS

2002/0114505 A1    8/2002    Mahon et al.

FOREIGN PATENT DOCUMENTS

| JP | 02-208545 A |   | 8/1990 |
|----|-------------|---|--------|
| JP | 4-104044    |   | 4/1992 |
| JP | 2002-2667   |   | 1/2000 |
| JP | 2000002667  | * | 1/2000 |
| JP | 2000002667 A| * | 1/2000 |
| JP | 2000028320  |   | 1/2000 |
| JP | 2000028320 A| * | 1/2000 |

OTHER PUBLICATIONS

Machine-generated English translation, JP 2000-002667 A, http://www4.inpit.go.jp/, Jun. 2008.*
Chinese Office Action with English translation.
Japanese Office Action.
Patent Abstracts of Japan, Mishiro Katsuyoshi, "Device for Inspecting Soldered Object for Appearance", U.S. Appl. No. 11/031,880; Publication Date: Feb. 2, 1999, 1 page.

* cited by examiner

IMAGE RECOGNITION APPARATUS AND METHOD FOR SURFACE DISCRIMINATION USING REFLECTED LIGHT

CROSS-REFERENCES TO RELATED APPLICATIONS

Benefit of priority of Japanese Patent Application No. 2001-003032 filed Jan. 9, 2003 and 2003-003033 filed Jan. 9, 2003 is claimed under 35 U.S.C. § 119.

BACKGROUND OF THE INVENTION

The present invention relates to an image recognition apparatus and an image recognition method in which an image of an object to be recognized is acquired and the image is subjected to a recognizing process.

In a field of producing electronic parts or devices, an image recognition method in which the images of objects to be recognized such as electronic parts or boards are picked up by a camera and the images as the image picked-up results are recognized to identify the objects to be recognized and detect positions has been widely employed. As an example to which the image recognition method is applied, a print inspection is performed for the boards after a solder printing carried out before the electronic parts are mounted. In the print inspection, the printed state of cream solder printed on an electrode of the board, that is, a printed position or an amount of printed solder or the like is detected by recognizing the image to decide whether or not the printed state is good. For example, it is proposed in JP-A-4-104044 or JP-A-2000-2667.

A certain electrode of the board may have a solder leveler with a solder film formed on the surface of the electrode in order to improve a solder joint property. When the cream solder printed on the electrode having such as older leveler is an object to be recognized, the cream solder has been hardly identified in accordance with an image recognition. Further, the electrode on the board and the cream solder on the electrode are hardly identified at the same time. That is, to identify the cream solder, the printed part of the cream solder needs to be separated from the surface of the solder leveler in accordance with a luminance difference. However, since the solder leveler and the cream solder include the naturally same material, an apparent luminance difference hardly appears on the picked up image. Thus, a highly accurate recognition has been difficult. Further, a plurality of images picked up under different illuminating conditions need to be obtained, so that much time has been required to obtain the images and a recognition tact time has been hardly shortened.

SUMMARY OF THE INVENTION

Thus, it is an object of the present invention to provide an image recognition apparatus and an image recognition method capable of improving recognition accuracy and provide an image recognition apparatus and an image recognition method capable of shortening a recognition tact time.

In an image recognition apparatus according to the present invention, an image obtained by picking up an image of an object to be recognized that includes a background surface, a first surface with a glossiness and a second surface with a glossiness lower than that of the first surface in a recognition surface, the first surface being partitioned by a rectangular boundary and the second surface being provided on the first surface in the background surface, is subjected to a recognition process to discriminate the first surface from the second surface in the background surface. The image recognition apparatus comprises: an illuminating part for applying illumination light to the object to be recognized upon picking up the image; a camera for receiving the reflected light of the illumination light to pickup the image of the object to be recognized; and a recognizing process part for recognizing image data obtained by the camera. The illuminating part applies the illumination light to the object to be recognized from a light applying direction in which regularly reflected light from the first surface is not received by the camera.

In an image recognition apparatus according to the present invention, an image obtained by picking up an image of an object to be recognized that includes a background surface, a first surface with a glossiness and a second surface with a glossiness lower than that of the first surface in a recognition surface, the first surface being partitioned by a rectangular boundary and the second surface being provided on the first surface in the background surface, is subjected to a recognition process to discriminate the first surface from the second surface in the background surface. The image recognition apparatus comprises: an illuminating part for applying illumination light to the object to be recognized upon picking up the image; a camera for receiving the reflected light of the illumination light to pick up the color image of the object to be recognized; and a recognizing process part for recognizing image data obtained by the camera. The illuminating part includes a first illuminating unit for applying white illumination light to the object to be recognized from a first light applying direction in which regularly reflected light from the first surface is not received by the camera and a second illuminating unit for applying colored illumination light to the object to be recognized from a second light applying direction in which the reflected light from the first surface is received by the camera.

In an image recognition method according to the present invention, an image obtained by picking up an image of an object to be recognized that includes a background surface, a first surface with a glossiness and a second surface with a glossiness lower than that of the first surface in a recognition surface, the first surface being partitioned by a rectangular boundary and the second surface being provided on the first surface in the background surface, is subjected to a recognition process to discriminate the first surface from the second surface in the background surface. The image recognition method comprises the step of: irradiating the object to be recognized with illumination light from a light applying direction in which regularly reflected light from the first surface is not received by the camera when the object to be recognized is irradiated with the illumination light by an illuminating part and the reflected light of the illumination light is received from an upper part to pick up the image of the object to be recognized.

In an image recognition method according to the present invention, an image obtained by picking up an image of an object to be recognized that includes a background surface, a first surface with a glossiness and a second surface with a glossiness lower than that of the first surface in a recognition surface, the first surface being partitioned by a rectangular boundary and the second surface being provided on the first surface in the background surface, is subjected to a recognition process to discriminate the first surface from the second surface in the background surface. The image recognition method comprises the steps of: irradiating the object to be recognized with white illumination light by a first illuminating unit from a first light applying direction in which regularly reflected light from the first surface is not received by the camera when the object to be recognized is irradiated with the illumination light by an illuminating part and the reflected light of the illumination light is received from an upper part to pick up the image of the object to be recognized; and irradiating the object to be recognized with colored illumination light by a second illuminating unit from a second light applying direction in which the reflected light from the first surface is received by the camera.

According to the present invention, when the object to be recognized is irradiated with the illumination lights by the illuminating part and the reflected lights of the illumination lights are received from the upper part to pick up the image of the object to be recognized, the object to be recognized is irradiated with the illumination lights from the light applying directions in which the regularly reflected lights from the first surface having the glossiness are not received by the camera. Thus, the first surface can be accurately separated from the second surface having the glossiness lower than that of the first surface.

Further, when the object to be recognized is irradiated with the illumination lights by the illuminating part and the reflected lights of the illumination lights are received from the upper part to pick up the image of the object to be recognized, the object to be recognized is irradiated with the white illumination lights by the first illuminating unit from the first light applying directions in which the regularly reflected lights from the first surface are not received by the camera and the object to be recognized is irradiated with the colored illumination lights by the second illuminating unit from the second light applying directions in which the reflected lights from the first surface are received by the camera. Thus, the first surface and the second surface can be identified on the same recognition screen from the image obtained by one image pick-up operation.

BRIEF DESCRIPTION OF THE DRAWINGS

FIG. 14(a) and 14 (b) show explanatory views of the light applying direction of the illumination light by the image pick-up unit of the image recognition apparatus according to one embodiment of the present invention.

DETAILED DESCRIPTION OF THE PREFERRED EMBODIMENTS

Figure 1:
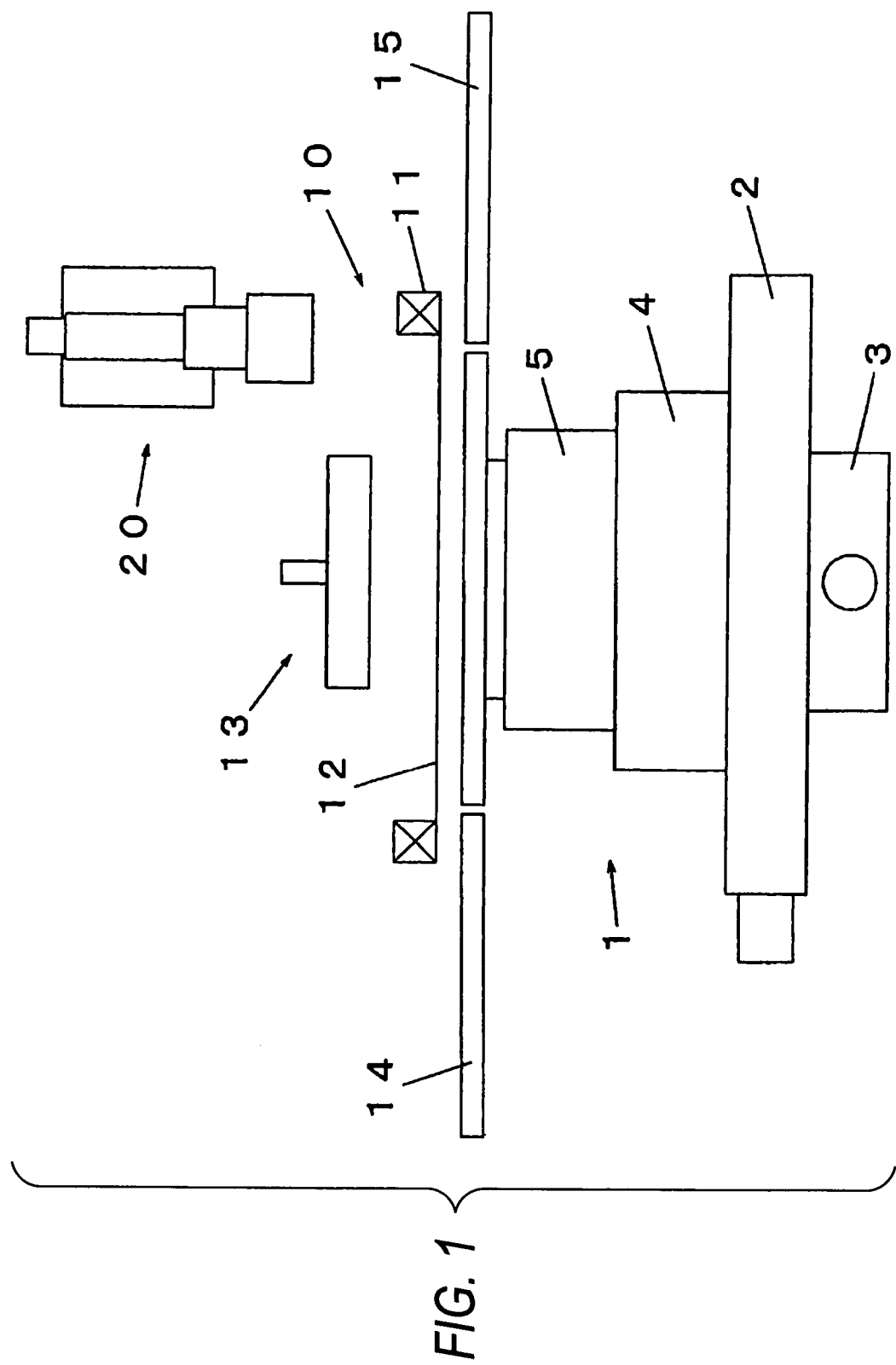
FIG. 1 is a front view of a screen process printing device according to one embodiment of the present invention.

Now, embodiments of the present invention will be described by referring to the drawings. Firstly referring to FIGS. 1, 2 and 3, the structure of the screen process printing device will be described. The screen process printing device has not only a printing mechanism for printing cream solder on a board on which electronic parts are mounted, but also a function as a print inspection device for deciding whether or not a printed state is good, as described below.

Figure 2:
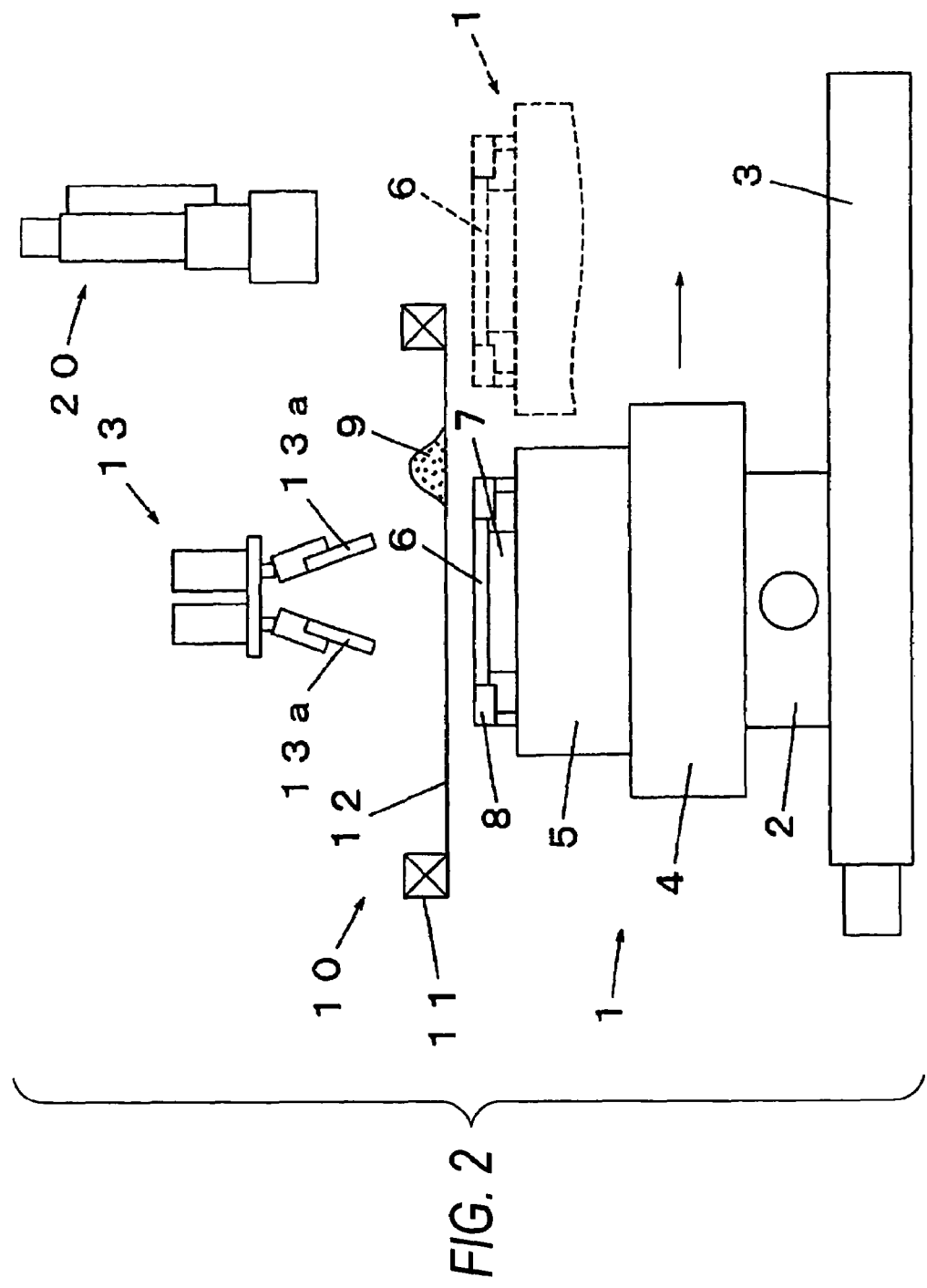
FIG. 2 is a side view of the screen process printing device according to one embodiment of the present invention.
Figure 3:
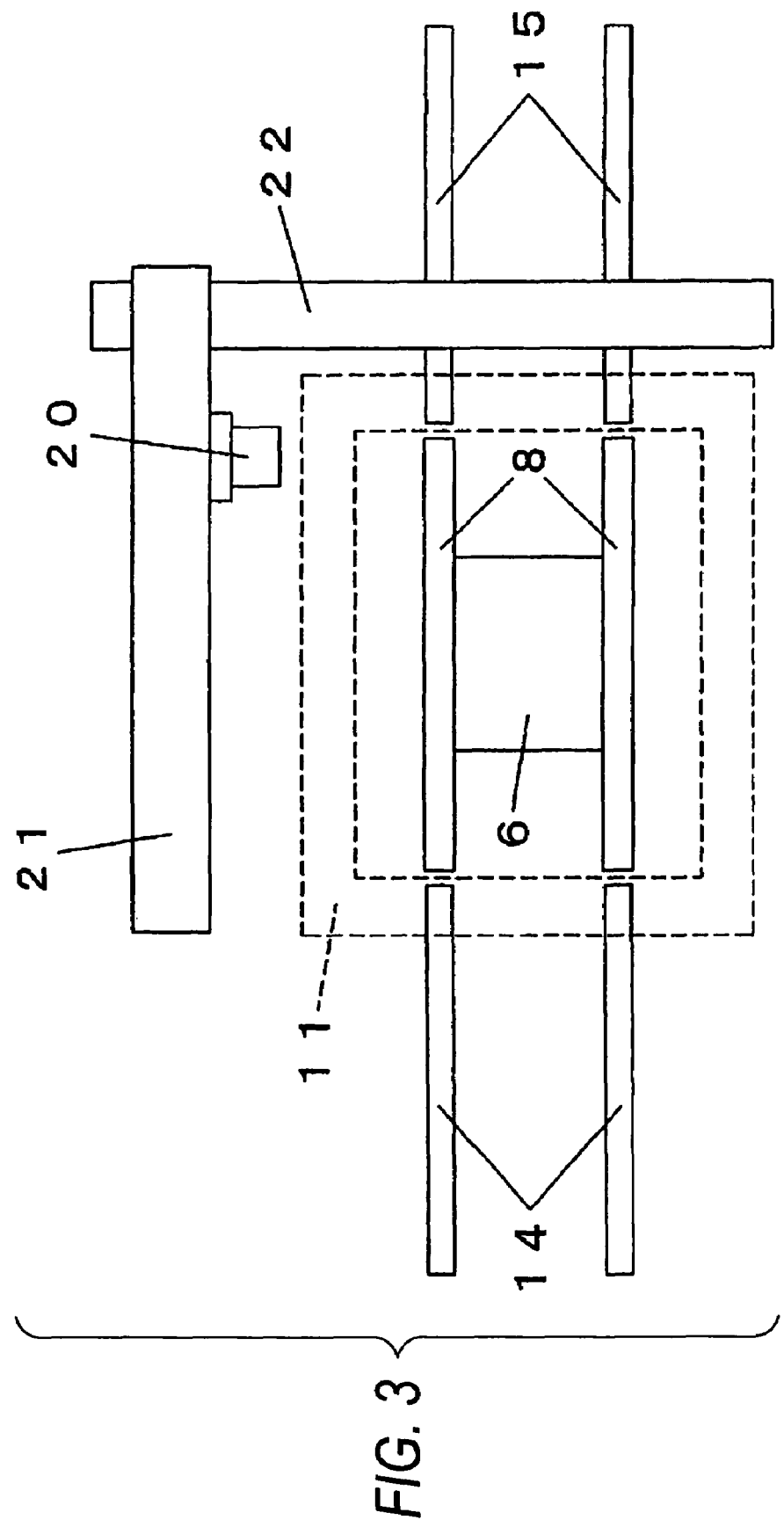
FIG. 3 is a plan view of the screen process printing device according to one embodiment of the present invention.

In FIGS. 1 and 2, a board positioning part 1 comprises a movable table having an X-axis table 2 and a Y-axis table 3, a θ-axis table 4 stacked thereon and a Z-axis table 5 disposed thereon. On the Z-axis table 5, a board holding part 7 for holding a board 6 held by a clamper 8 from a lower part is provided. The board 6 to be printed is conveyed to the board positioning part 1 by a loading conveyor 14 shown in FIGS. 1 and 3. The board positioning part 1 is driven so that the board 6 moves in XY directions and is positioned at a printing position and a board recognizing position described below. The board 6 on which printing has been subjected is delivered by an unloading conveyor 15.

Figure 5:
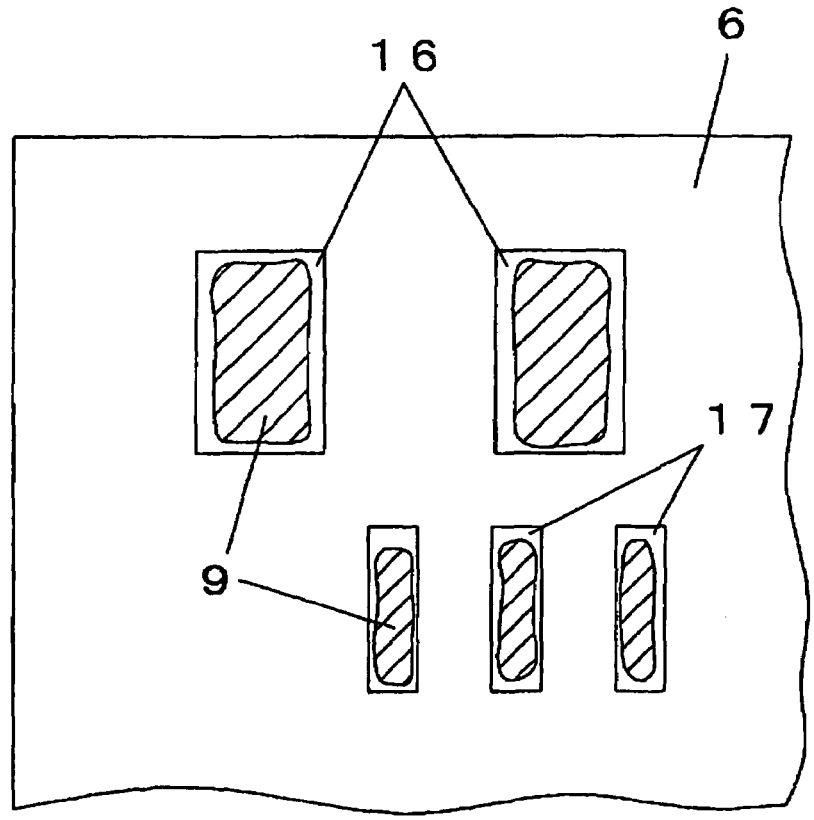
FIG. 5(a) is a plan view of a board as an object to be recognized of an image recognition apparatus according to one embodiment of the present invention.
FIG. 5(b) is a partial sectional view of the board as the object to be recognized of the image recognition apparatus according to one embodiment of the present invention.
Figure 5:
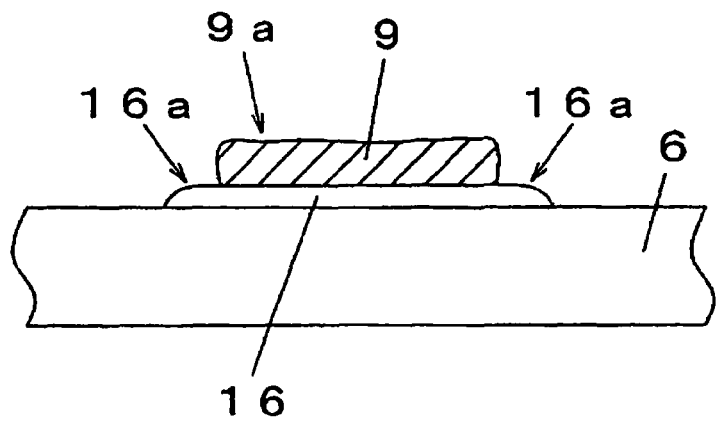

A screen mask 10 is disposed above the board positioning part 1. The screen mask 10 includes a mask plate 12 mounted on a holder 11. The board 6 is aligned with the mask plate 12 by the board positioning part 1 and abuts thereon from a lower part. In the surface of the board 6 on which a circuit is formed, rectangular electrodes 16 and 17 for connecting electronic parts are provided as shown in FIG. 5(a). On the surfaces of the electrodes 16 and 17, solder levelers are formed and solder leveler forming surfaces 16a serve as first surfaces with glossiness.

On the screen mask 10, a squeegee head 13 is provided so as to freely reciprocate in the horizontal direction. While the board 6 abuts on the lower surface of the mask plate 12, cream solder 9 is supplied to the mask plate 12 and squeegees 13a of the squeegee head 13 are allowed to abut on the surface of the mask plate 12 and slide. Thus, the cream solder 9 is printed on the printing surface of the board 6 through pattern holes provided in the mask plate 12. As shown in FIG. 5(a), the cream solder 9 is printed on the solder leveler forming surfaces 16a of the electrodes 16 and 17. The solder surface 9a of the cream solder 9 under a printed state serves as a second surface with a glossiness lower than that of the solder leveler forming surface 16a.

Figure 4:
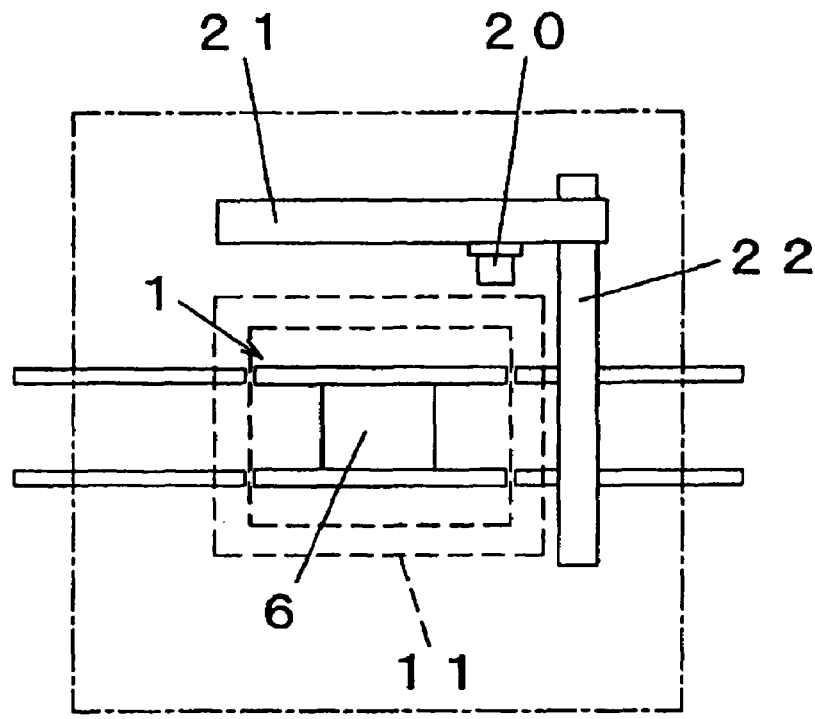
FIGS. 4(a) and 4(b) are partial plan views of a board print surface by the screen process printing device according to one embodiment of the present invention.
Figure 4:
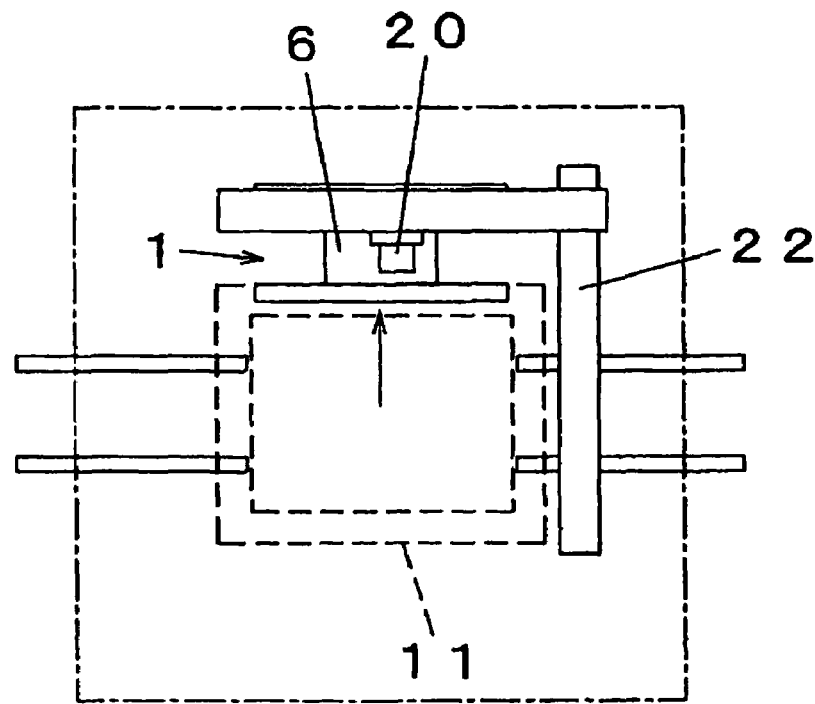

On the screen mask 10, an image pick-up unit 20 as image pick-up means is provided. As shown in FIG. 4(a), the image pick-up unit 20 moves in X and Y directions by an X-axis table 21 and a Y-axis table 22. The X-axis table 21 and the Y-axis table 22 serve as image pick-up moving means for moving the image pick-up unit 20. The image pick-up unit 20 is moved relative to the mask plate 12 by the image pick-up moving means so that the image pick-up unit 20 picks up the image of an arbitrary position of the mask plate 12.

The board positioning part 1 moves in the direction of Y from the lower part of the screen mask 10 by the Y-axis table 3 as shown in FIG. 4(b) to move the held board 6 to a board recognizing position (also see FIG. 2). Under this state, the image pick-up unit 20 is moved to the board 6 on the board positioning part 1. Thus, the image pick-up unit 20 can pick up the arbitrary position of the board 6. A print inspection after a screen process printing is carried out by picking up the image of the board 6 on which the solder is printed as an object to be recognized by the image pick-up unit 20.

In the print inspection, as shown in FIG. 5(b), the electrodes 16 and 17 are partitioned from the surface of the board 6 by rectangular boundaries and protrude upward by the thickness of solder levelers in the board 6 as the object to be recognized. Further, the cream solder 9 is printed on each solder leveler forming surface 16a. Specifically, the image picked up by the image pick-up unit 20 serves as a recognition surface in recognizing the image for the print inspection. The recognition surface includes a background surface as the surface of the board 6, the solder leveler forming surface 16a (first surface) and the solder surface 9a (second surface) of the cream solder 9 printed on the solder leveler forming surface 16a. In a recognizing process for the print inspection, the solder leveler forming surface 16a is discriminated from the solder surface 9a in the background surface to obtain a solder print area. Then, the solder print area is compared with a preset inspecting threshold value to decide whether or not a printed state is good.

Figure 6:
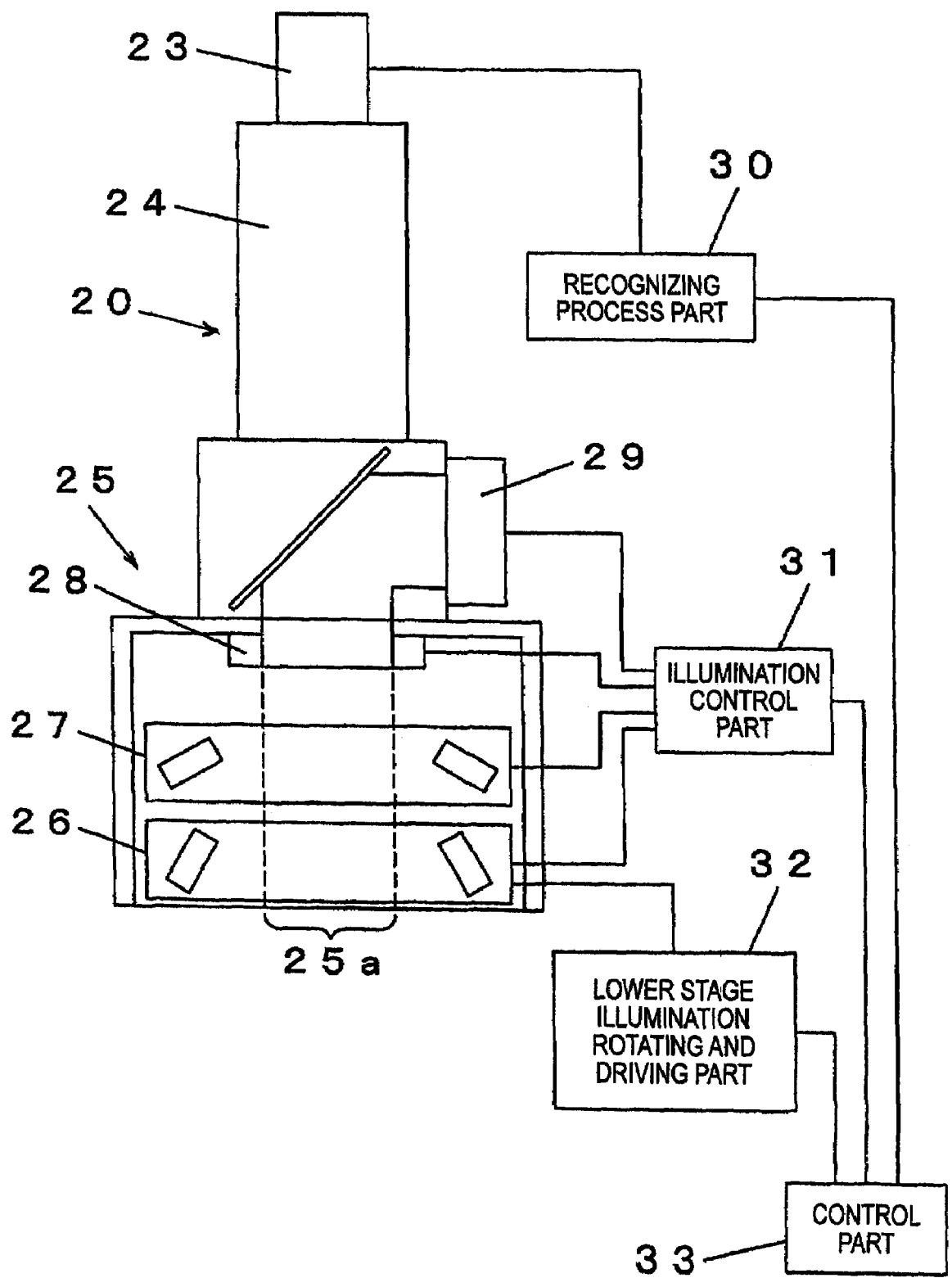
FIG. 6 is a sectional view of an image pick-up unit of the image recognition apparatus according to one embodiment of the present invention.

Now, referring to FIG. 6, the structure of the image pick-up unit 20 will be described. As shown in FIG. 6, in the image pick-up unit 20, a zoom optical system 24 is connected to a camera 23 capable of picking up a color image and an illuminating part 25 is disposed below the zoom optical system 24. The illuminating part 25 applies illumination lights to the surface of the board 6 as the object to be recognized upon picking up the image. The camera 23 receives the reflected lights of the lights applied by the illuminating part 25 and reflected by the board 6 from an upper part through the zoom optical system 24 to pick up the image of the object to be recognized. The image data of the recognition surface obtained by the camera 23 undergoes a recognizing process by a recognizing process part 30 and the recognized result is supplied a control part 33.

Now, the structure of the illuminating part 25 will be described. The illuminating part 25 includes a plurality of illuminating units having a lower stage illuminating unit 26, an intermediate stage illuminating unit 27, an upper stage illuminating unit 28 and a coaxial illuminating unit 29, which are described below, to irradiate the board 6 located in the lower part with illumination lights under various kinds of illuminating conditions. These illuminating units are controlled by the control part 33 through an illumination control part 31.

In this case, the lower stage illuminating unit 26, the intermediate illuminating unit 27 and the upper stage illuminating unit 28 are respectively ring shaped illuminating units in which light sources are arranged around circular image pick-up ranges 25a by the camera 23. The lower stage illuminating unit 26 of these illuminating units can rotate by a prescribed angle about the image pick-up range 25a by a lower stage illumination rotating and driving part 32. The image pick-up unit 20, the recognizing process part 30, the illumination control part 31 and the lower stage illumination rotating and driving part 32 constitute an image recognition apparatus for carrying out a recognizing process for picking up the image of the board in the screen process printing device to inspect the print.

Figure 7:
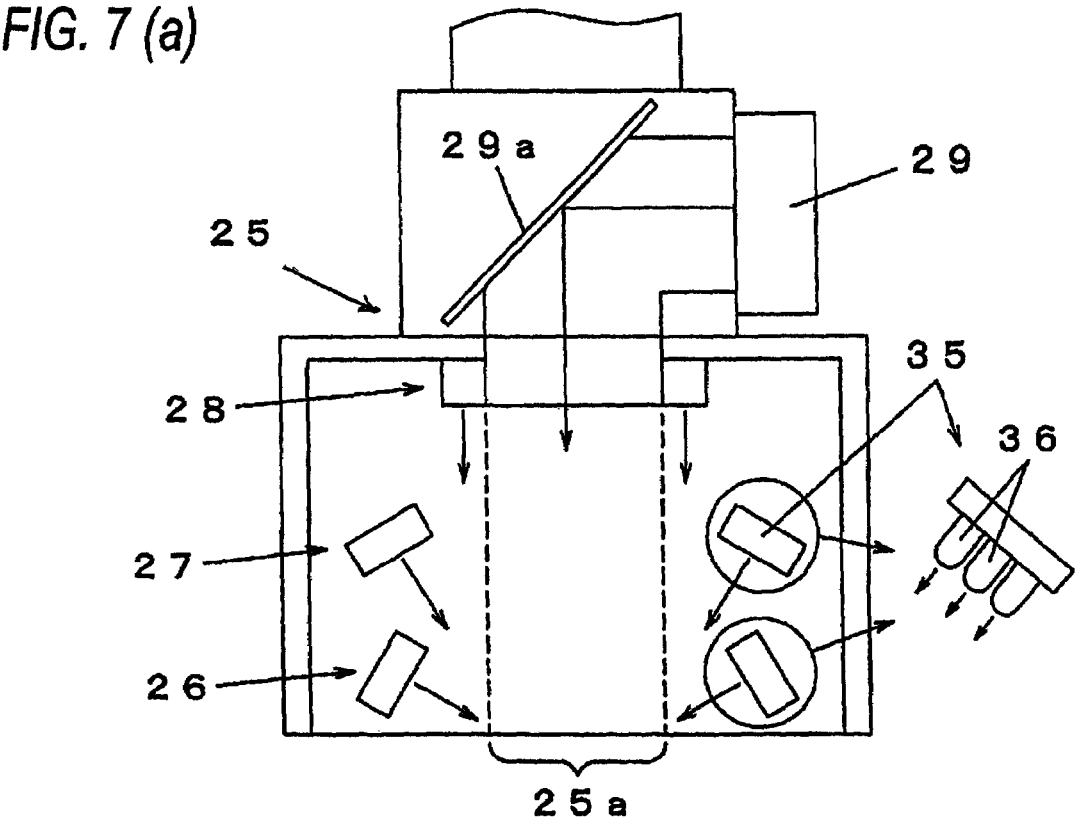
FIG. 7(a) is an explanatory diagram of the structure of an illuminating part of the image pick-up unit of the image recognition apparatus according to one embodiment of the present invention.
FIG. 7(b) is an explanatory diagram of the light applying direction of the illumination light by the image pick-up unit of the image recognition apparatus according to one embodiment of the present invention.
Figure 7:
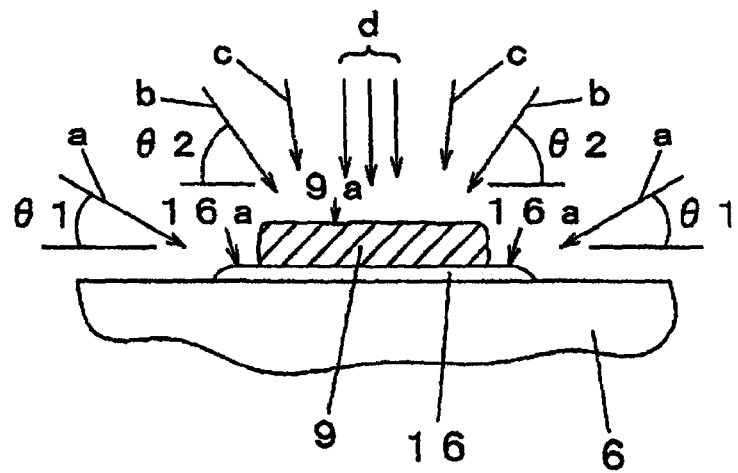

Now, referring to FIG. 7, the illuminating function of each of the illuminating units will be described. In the lower stage illuminating unit 26 and the intermediate stage illuminating unit 27, light source parts 35 respectively having a plurality of LEDs 36 are arranged in the radial directions around the image pick-up ranges 25a. Here, the lower stage illuminating unit 26 and the intermediate illuminating unit 27 respectively apply illumination lights to objects to be recognized located within the image pick-up ranges 25a at illumination angles of θ1 and θ2 (angles formed by the light applying directions of the illumination lights and a horizontal direction (surface of the board 6)) from directions shown by arrow marks a and b, as shown in FIG. 7(b).

The upper stage illuminating unit 28 has a light source part composed of LEDs arranged in a ring form in a part above the intermediate stage illuminating unit 27 and applies illumination lights to an object to be recognized located within the image pick-up range 25a from an upper part. Further, the coaxial illuminating unit 29 is located in the side of a half mirror 29a disposed below the zoom optical system 24. Illumination lights horizontally applied from a light source part composed of LEDs are reflected downward by the half mirror 29a to illuminate an object to be recognized from a coaxial direction.

Figure 8:
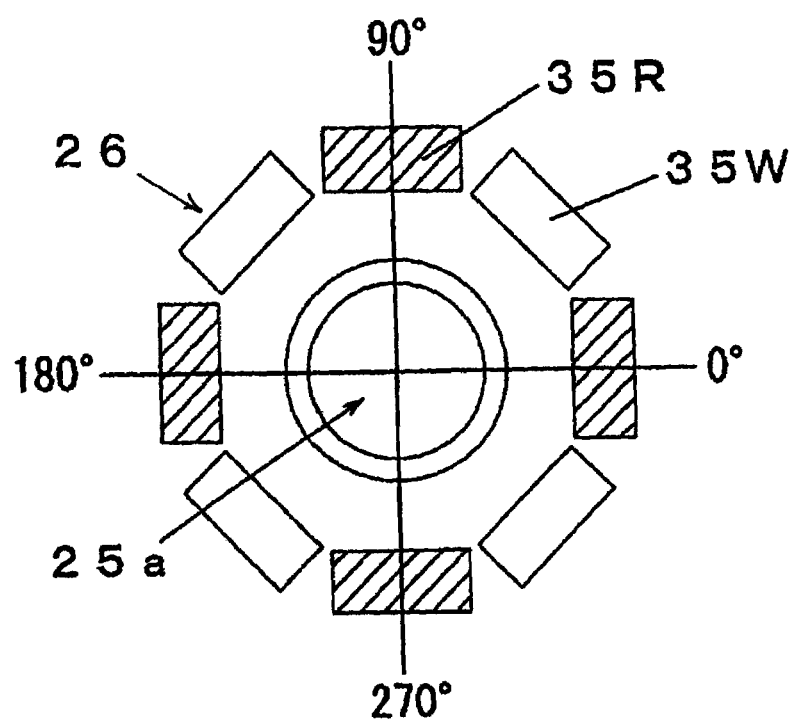
FIGS. 8(a) and 8(b) are explanatory views of the arrangement of a light source of the image pick-up unit of the image recognition apparatus according to one embodiment of the present invention.
Figure 8:
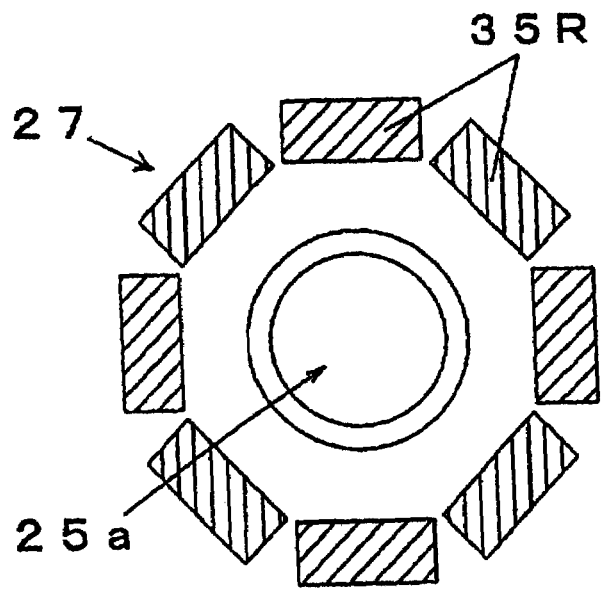

Now, the illumination light applied from each of the illuminating units will be described. FIGS. 8(a) and 8(b) respectively show horizontal positions of the light source parts in the lower stage illuminating unit 26 and the intermediate stage illuminating unit 27. In each of the lower stage illuminating unit 26 and the intermediate stage illuminating unit 27, eight light source parts are arranged in the radial directions about the image pick-up position 25a. The illumination light is applied to the center of the image pick-up position 25a from each of the light source parts.

As shown in FIG. 8(a), in the four directions of 0°, 90°, 180°, and 270° of the eight light source parts disposed in the lower stage illuminating unit 26, red color light source parts 35R having the LEDs emitting red color lights are arranged. In four directions forming angles of 45° with the red color light source parts 35R, white color light source parts 35W having the LEDs emitting white color lights are arranged.

Accordingly, when the lower stage illuminating unit 26 is lighted, the electrode 16 formed on the surface of the board 6 in a horizontal position and the cream solder 9 formed on the electrode 16 are irradiated with the white color lights and the red color lights from the directions of the illumination angles of θ1 (see arrow marks a), as shown in FIG. 7(b). At this time, as described above, the white color lights and the red color lights are respectively applied only from the determined directions within a horizontal plane. The attaching direction of each of the light source parts in the lower stage illuminating unit 26 is set so that the illumination angle θ1 is 45° or smaller.

As shown in FIG. 8(b), the eight light source parts arranged in the intermediate stage illuminating unit 27 are the red color light source parts 35R all having the LEDs emitting the red color lights. When the intermediate stage illuminating unit 27 is lighted, the electrode 16 formed on the surface of the board 6 in a horizontal position and the cream solder 9 on the electrode 16 are irradiated with the red color lights at the illumination angles of θ2 from all the circumference directions (see arrow marks b), as shown in FIG. 7(b).

In the upper stage illuminating unit 28 and the coaxial illuminating unit 29, light source parts respectively having LEDs emitting red color lights are arranged. When the upper stage illuminating unit 28 is lighted, the electrode 16 formed on the surface of the board 6 and the cream solder 9 on the electrode 16 are irradiated with red color lights from slightly inclined directions (see arrow marks c) relative to a vertical direction, as shown in FIG. 7(b). Further, when the coaxial illuminating unit 29 is lighted, red color lights reflected downward by the half mirror 29a are applied to the electrode and the cream solder from coaxial directions (see arrow marks d).

The image recognition apparatus is formed as described above. Now, an image recognition method carried out for the purpose of a print inspection for the board on which the cream solder is printed as an object will be described below. In the image recognition method, the solder leveler forming surface 16a is discriminated from the solder surface 9a in the background surface of a screen obtained by picking up the image of the surface of the board 6 to obtain the solder print area. Then, the solder print area is compared with a preset inspecting threshold value to decide whether or not the printed state is good.

(First Mode of the Embodiment)

Upon print inspection, a printed board 6 is moved to an image pick-up position and an image pick-up unit 20 is positioned on the position of the board 6 to be inspected. At this time, as shown in FIG. 9(a), an alignment is carried out so that the outlines of four sides of a rectangular electrode 16 on which a cream solder 9 is printed, that is, boundaries on the surface of the board 6 respectively substantially correspond to the directions of 0°, 90°, 180° and 270°.

Then, when an image is picked up by a camera 23, only a lower stage illuminating unit 26 is used. Further, only four white light source parts 35W of eight light source parts are lighted to pick up the image of the position on the board 6 to be inspected. In this image pick-up, as shown in FIG. 9(b), the solder surface 9a of the cream solder 9 and a solder leveler surface 16a are irradiated with white color lights from directions shown by arrow marks a (see FIG. 7(b)). The illumination lights (see arrow marks a1) of these illumination lights with which the solder surface 9a is irradiated are irregularly reflected by the solder surface 9a with a low glossiness. The irregularly reflected lights are received by the upper camera 23 (see FIG. 6).

Then, in the illumination lights (see arrow marks a2) with which the solder leveler surface 16a is irradiated, corresponding parts are substantially regularly reflected by the solder leveler surface 16a with a glossiness in specific directions corresponding to illuminating directions (angle θ3) in a horizontal plane. At this time, the light applying directions of the illumination lights emitted from the white color light source parts 35W in the horizontal plane are substantially set to directions of 45° relative to the boundaries of the electrode 16. Thus, the reflecting directions of the regularly reflected lights in the horizontal plane are biased as shown in broken line arrow marks in FIG. 9(c). Accordingly, the regularly reflected lights are not received by the upper camera 23. Then, only the solder leveler forming surfaces 16a in the corner parts of the electrode 16 regularly reflect upward the illumination lights from oblique directions and the regularly reflected lights are received by the camera 23. Here, while θ3 is set to 45°, an angle at which the regularly reflected lights are not received by the camera 23 may be employed and the angle may be set to 75° or smaller under practical conditions.

Figure 12:
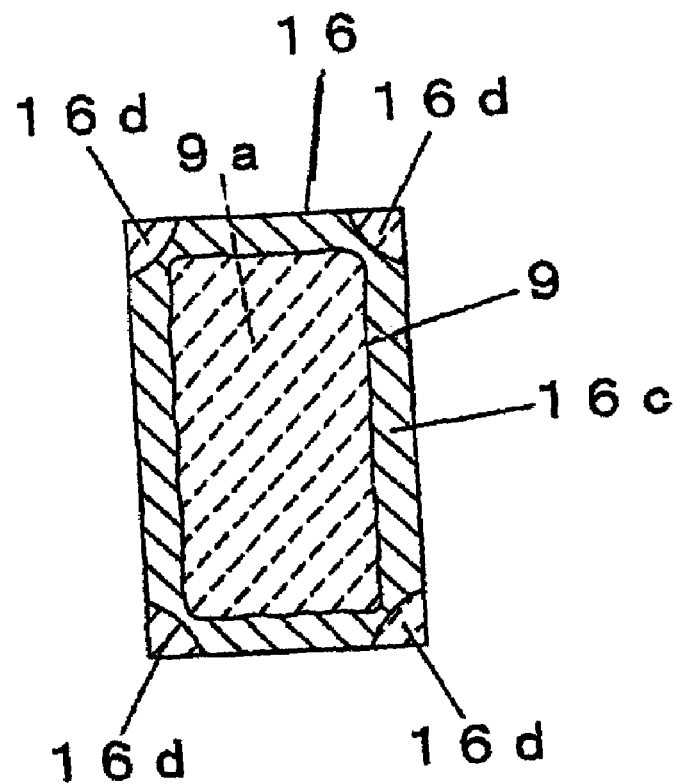
FIGS. 12(a) and 12(b) are views of an obtained image of the image recognition apparatus according to one embodiment of the present invention.
Figure 12:
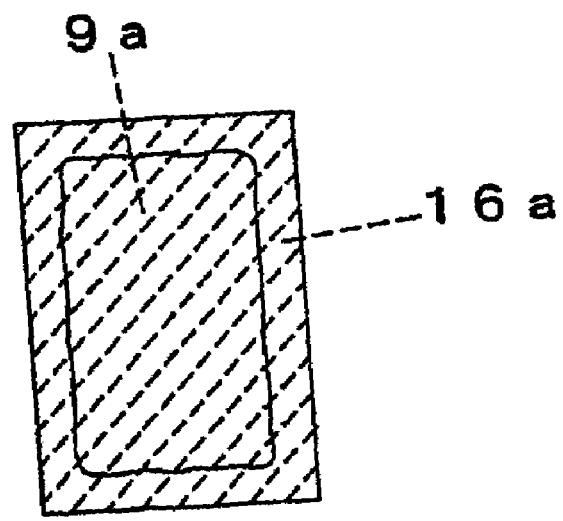

FIG. 12(a) shows a recognition surface obtained by picking up the image under the above-described illuminating conditions. This recognition surface has the image including the electrode 16 and the cream solder 9 printed on the electrode 16 in a background surface showing the surface of the board 6. In FIG. 12(a), leveler parallel parts 16c of parts corresponding to the solder leveler forming surface 16a of the electrode 16 have illuminating conditions under which the regularly reflected lights of the white color illumination lights are not received by the camera 23 as described above, they have low luminance on a screen. Only the corner parts 16d of the electrode are high in their luminance in which the regularly reflected lights are received by the camera as described above.

Accordingly, the irregularly reflected lights of a solder surface 9a are received so that the solder part 9 whose image is picked up with a certain degree of luminance can be clearly separated from the leveler parallel parts 16c on the image due to a luminance difference and the cream solder 9 on the electrode 16 on which the solder leveler is formed can be identified with high accuracy.

FIG. 12(b) shows a recognition screen obtained by a usual image recognition method, for comparison, in which white color illumination lights are applied from all directions when an electrode 16 on which a cream solder 9 is likewise printed is used as an object to be recognized. In this case, since the illumination lights are incident on a solder leveler surface 16a not only from oblique directions, but also from normal directions, regularly reflected lights from the solder leveler surface 16a with a glossiness are incident on a camera 23. Therefore, the solder leveler surface 16a is taken substantially completely or partly as an image with high luminance. Accordingly, since the luminance difference between the image and an image receiving the irregularly reflected lights of the cream solder 9 is obscure, the cream solder 9 on the electrode 16 is obscurely identified.

As described above, in the image recognition method according to this embodiment, the board 6 that has the solder leveler forming surface 16a partitioned by the rectangular boundary on the surface of the board and the cream solder 9 printed on the solder leveler forming surface 16a is provided as the object to be recognized. Then, the upper surface of the board 6 as the recognition surface for the object to be recognized by the image pick-up unit 20 includes the electrode 16 having the solder leveler forming surface 16a as a first surface with the glossiness and the solder surface 9a as a second surface with the glossiness lower than that of the solder leveler forming surface 16a in the surface of the board 6 as the background surface.

When the upper surface of the board 6 is irradiated with the illumination lights by an illuminating part 25 and the reflected lights of the illumination lights are received from the upper part to pick up the image of the upper surface of the board 6, the upper surface of the board 6 is irradiated with the illumination lights from the light applying direction in which the regularly reflected lights from the solder leveler surface 16a are not received by the camera 23. Specifically, as shown in FIG. 7(b), the upper surface of the board is irradiated with the white illumination lights from a direction in which an illumination angle of θ1 formed by the light applying direction to the solder leveler surface 16a and the surface of the board 6 is 45° or smaller in a vertical plane, and as shown in FIG. 9(c), from a direction in which an angle of θ3 formed by the light applying direction to the solder leveler surface 16*a* and the boundary of the electrode 16 is 75° or smaller in a horizontal plane.

Thus, the solder leveler surface 16*a* and the solder surface 9*a* can be identified in accordance with an obvious luminance difference. Even when the cream solder 9 naturally including the naturally same material is printed on the solder leveler surface 16*a*, a recognition accuracy can be improved to detect a solder area with high accuracy.

Figure 14:
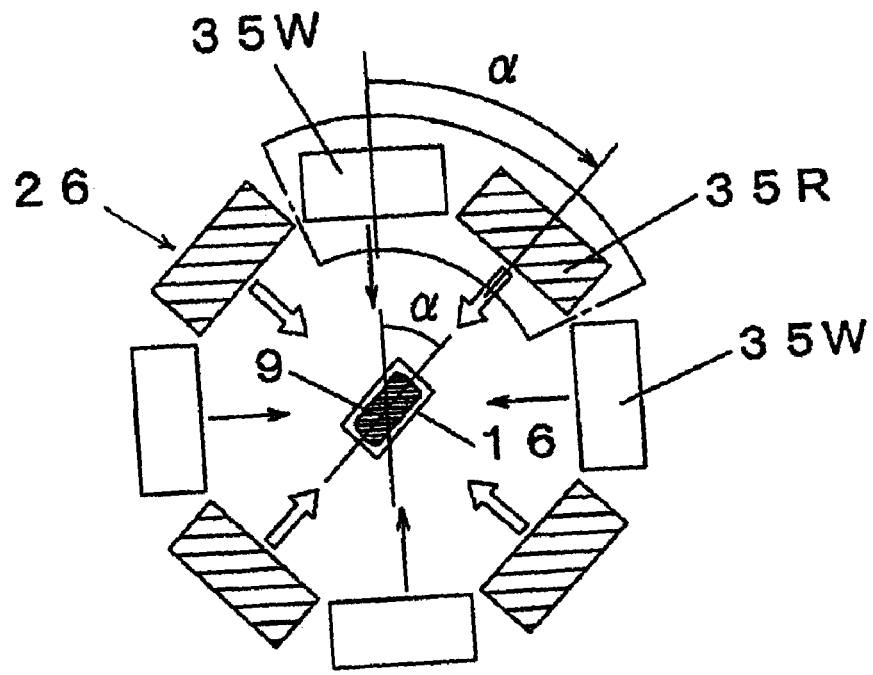
Figure 14:
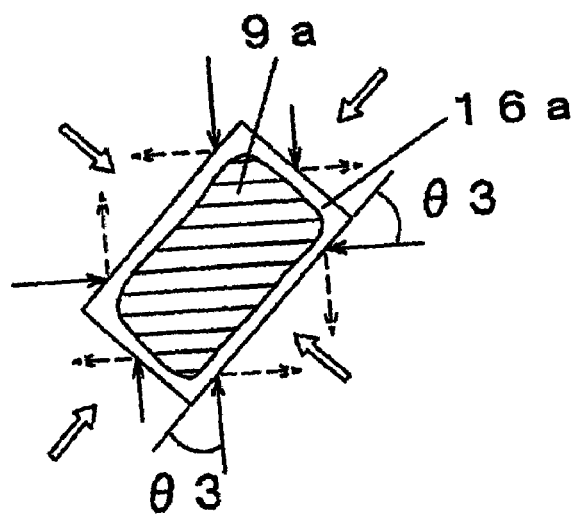

In the above-described embodiment, the example that the alignment is carried out in such a way that the boundaries of four sides showing the external form of the electrode 16 respectively substantially correspond to the directions of 0°, 90°, 180°, and 270° is described. However, as shown in FIG. 14(*a*), when the direction of the electrode 16 on the board 6 is inclined by an angle of α from a state shown in FIG. 9(*a*), a lower illuminating unit 26 is rotated by the same angle of α by a lower stage illumination rotating and driving part 32 (see FIG. 6). Thus, as shown in FIG. 14(*b*), white illumination lights are applied to the solder leveler forming surface from the same light applying direction as that of the example shown in FIG. 9(*c*).

Further, the above-described embodiment shows the example that the board 6 in which the cream solder 9 is printed on the electrode 16 having the solder leveler forming surface 16*a* serves as the object to be recognized. However, the present invention may be applied to other combinations than the above-described object to be recognized and an object to be recognized including a background surface, a first surface with a glossiness and a second surface with a glossiness lower than that of the first surface in a recognition surface, the first surface being partitioned by a rectangular boundary in the background surface and the second surface being provided on the first surface.

(Second Mode of Embodiment)

Figure 9:
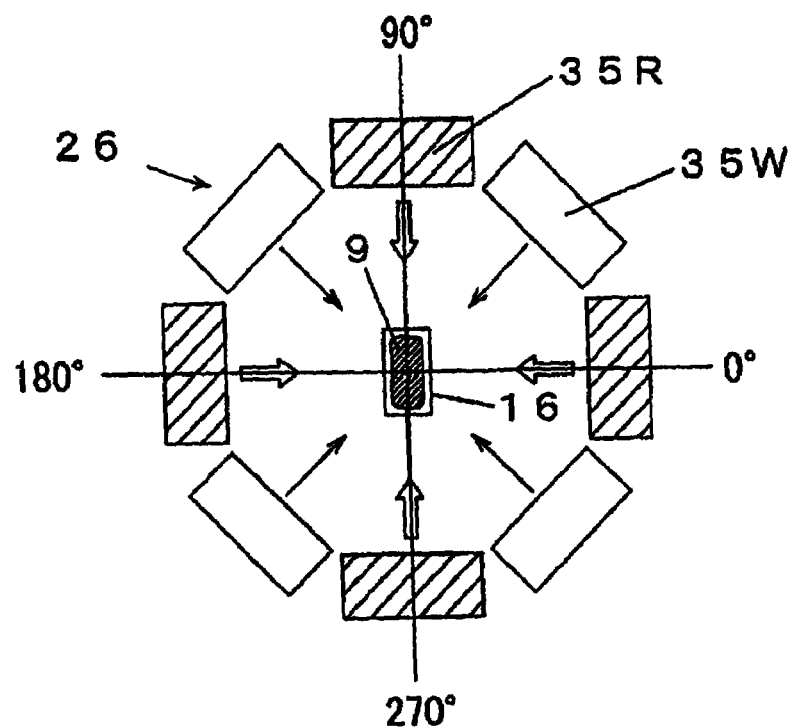
FIGS. 9(a) to 9(c) are explanatory views of the light applying direction of the illumination light by the image pick-up unit of the image recognition apparatus according to one embodiment of the present invention.
Figure 9:
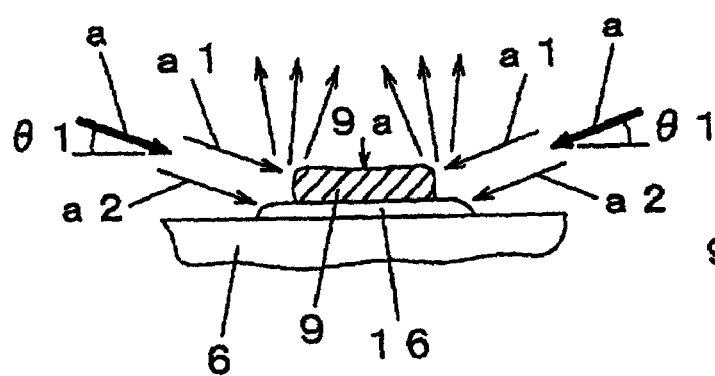
Figure 9:
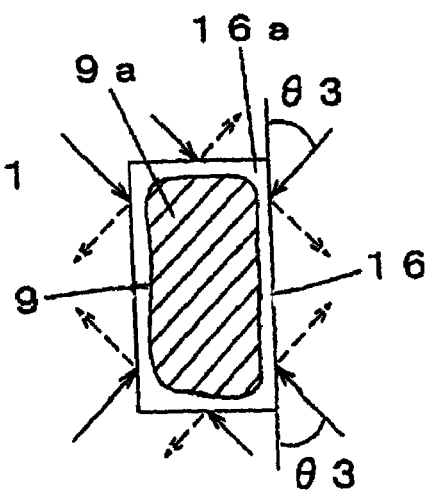

Upon print inspection, a printed board 6 is moved to an image pick-up position and an image pick-up unit 20 is positioned on the position of the board 6 to be inspected. At this time, as shown in FIG. 9(*a*), an alignment is carried out so that the outlines of four sides of a rectangular electrode 16 on which a cream solder 9 is printed, that is, boundaries on the surface of the board 6 respectively substantially correspond to the directions of 0°, 90°, 180° and 270°.

Then, when an image is picked up by a camera 23, a lower stage illuminating unit 26, an intermediate stage illuminating unit 27 and an upper stage illuminating unit 28 are used together. Firstly, the illuminating state of the lower stage illuminating unit 26 will be described. As shown in FIG. 9(*a*), upon picking up the image, all of four white color light source parts 35W and four red color light source parts 35 are lighted to irradiate the position of the board 6 to be inspected with illumination lights. FIG. 9(*b*) shows the reflected states of white illumination lights emitted from the white color light source parts 35W. The solder surface 9*a* of a cream solder 9 and a solder leveler surface 16*a* are irradiated with the white color illumination lights emitted from directions shown by arrow marks a (see FIG. 7(*b*)). The illumination lights (see arrow marks a1) of these illumination lights with which the solder surface 9*a* is irradiated are irregularly reflected by the solder surface 9*a* with a low glossiness and the irregularly reflected lights are received by the upper camera 23 (see FIG. 6).

Then, in the illumination lights (see arrow marks a2) with which the solder leveler surface 16*a* is irradiated, corresponding parts are regularly reflected by the solder leveler surface 16*a* with a glossiness in specific directions corresponding to light applying directions (angle θ3) in a horizontal plane. At this time, the light applying directions of the illumination lights emitted from the white color light source parts 35W in the horizontal plane are substantially set to directions of about 45° relative to the boundaries of the electrode 16. Thus, the reflecting directions of the regularly reflected lights in the horizontal plane are biased as shown in broken line arrow marks in FIG. 9(*c*). Accordingly, the regularly reflected lights are not received by the upper camera 23. Here, while θ3 is set to 45°, an angle at which the regularly reflected lights are not received by the camera 23 may be employed and the angle may be set to 75° or smaller under practical conditions.

Figure 10:
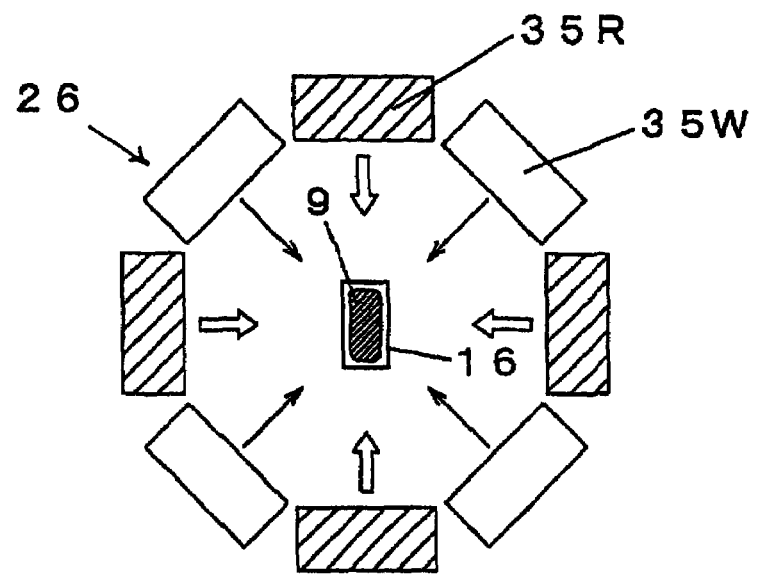
FIGS. 10(a) and 10(b) are explanatory view of the light applying direction of the illumination light by the image pick-up unit of the image recognition apparatus according to one embodiment of the present invention.
Figure 10:
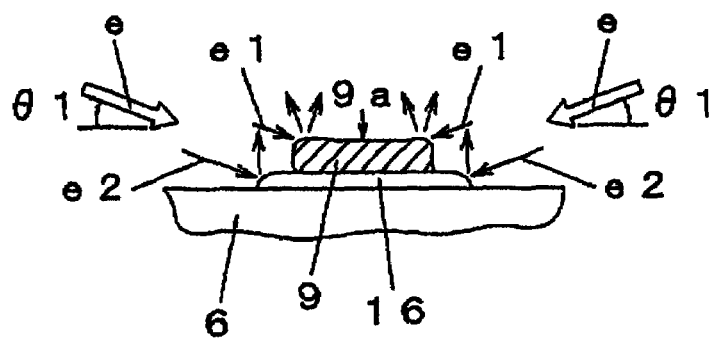

FIG. 10 shows the incident directions and the reflected conditions of red color illumination lights emitted from the red color light source parts 35R. As shown in FIG. 10(*a*), these red illumination lights are incident on the boundaries of the four sides of the rectangular electrode 16 from normal directions. As shown in FIG. 10(*b*), the solder surface 9*a* of the cream solder 9 and the solder leveler surface 16*a* are irradiated with the red color illumination lights applied from directions shown by arrow marks e.

The illumination lights of these illumination lights (see arrow marks e1) with which the solder surface 9*a* is irradiated are irregularly reflected by the solder surface 9*a* with the low glossiness and the irregularly reflected lights are received by the upper camera 23 (see FIG. 6). In the illumination lights (see arrow marks e2) with which the solder leveler surface 16*a* is irradiated, corresponding parts are regularly reflected by the solder leveler surface 16*a* with the glossiness in specific directions corresponding to incident angles. A part of the regularly reflected lights is reflected upward and received by the camera 23.

Figure 11:
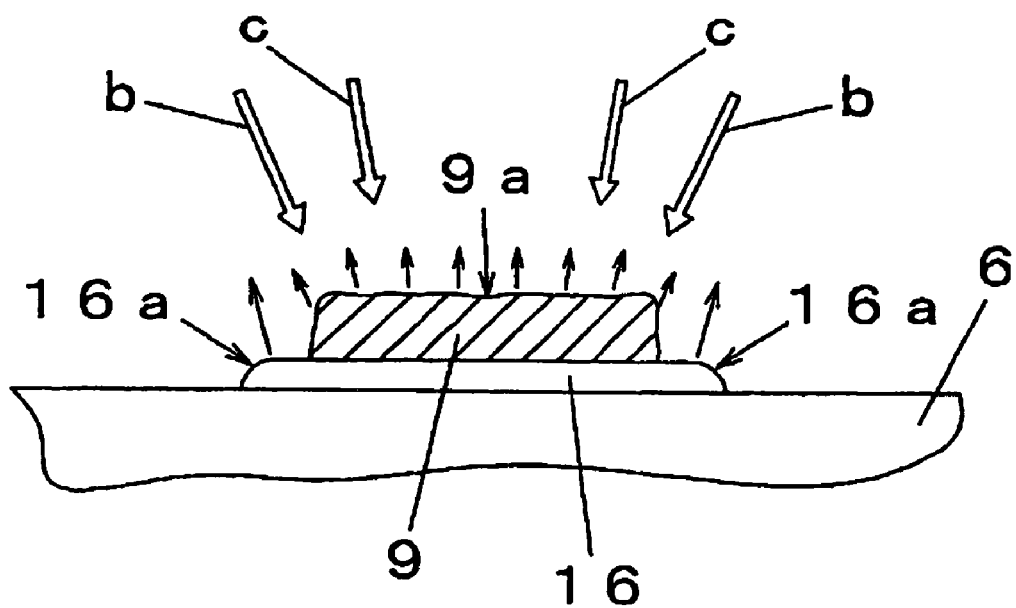
FIG. 11 is an explanatory view of the light applying direction of the illumination light by the image pick-up unit of the image recognition apparatus according to one embodiment of the present invention.

FIG. 11 shows the reflected conditions of illumination lights applied by the intermediate stage illuminating unit 27 and the upper stage illuminating unit 28. When an image is picked up, both the intermediate stage illuminating unit 27 and the upper stage illuminating unit 28 respectively apply red color illumination lights to the solder surface 9*a* of the cream solder 9 and the solder leveler surface 16*a* from directions of arrow marks b and c. The illumination lights of these illumination lights with which the solder surface 9*a* is irradiated are irregularly reflected by the solder surface 9*a* with the low glossiness and the irregularly reflected lights are likewise received by the upper camera 23. Further, in the illumination lights with which the solder leveler surface 16*a* is irradiated, corresponding parts are regularly reflected upward by the solder leveler surface 16*a* with the glossiness and received by the camera 23.

Figure 13:
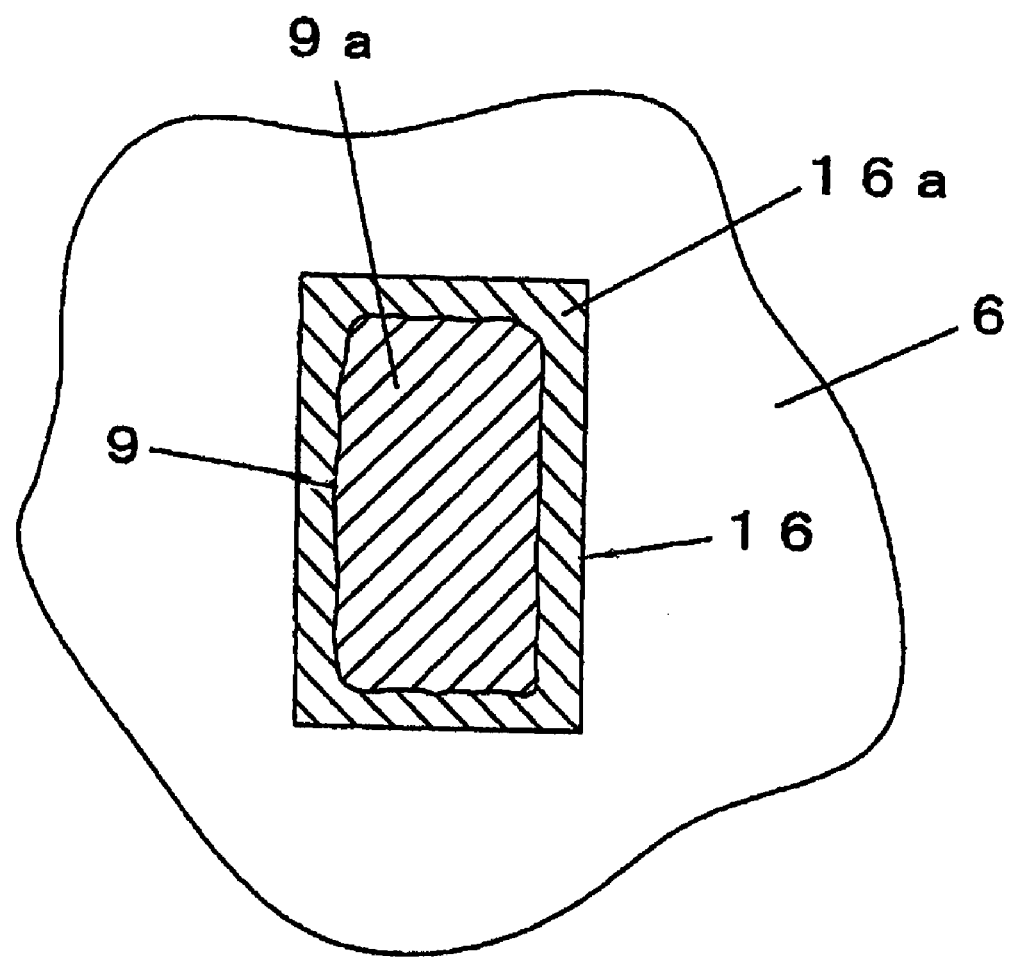
FIG. 13 is a view of an obtained image of the image recognition apparatus according to one embodiment of the present invention.

FIG. 13 shows a recognition screen obtained by picking up an image under the above-described illuminating conditions. This recognition screen shows a color image including an electrode 16 and a cream solder 9 printed on the electrode 16 in a background surface showing the surface of a board 6. In FIG. 13, the solder leveler forming surface 16*a* of the electrode 16 appears as a red colored part with the regularly reflected lights of red color illumination lights emitted from the lower stage illuminating unit 26, the intermediate stage illuminating unit 27 and the upper stage illuminating unit 28. Here, the solder leveler forming surface 16*a* is also irradiated with the white color illumination lights of the lower stage illuminating unit 26. However, since the regularly reflected lights of the white color illumination lights are reflected to the directions which are not received by the camera 23, as described above, the solder leveler forming surface 16*a* does not light with high luminance by the white color illumination lights.

On the contrary, the solder surface 9a of the cream solder 9 reflects upward the irregularly reflected lights of white color illumination lights emitted from the lower stage illuminating unit 26 and the irregularly reflected lights of the red color illumination lights emitted from the lower stage illuminating unit 26, the intermediate stage illuminating unit 27 and the upper stage illuminating unit 28. The camera 23 receives the irregularly reflected lights so that the cream solder 9 appears as a white colored part slightly including a red color and can be obviously discriminated from the solder leveler surface 16a appearing as a red colored part.

As described above, in the image recognition method according to this embodiment, the board 6 that has the solder leveler forming surface 16a partitioned by the rectangular boundary on the surface of the board and the cream solder 9 printed on the solder leveler forming surface 16a is provided as the object to be recognized. Then, the upper surface of the board 6 as the recognition surface of the object to be recognized by the image pick-up unit 20 includes the electrode 16 having the solder leveler forming surface 16a as a first surface with the glossiness and the solder surface 9a as a second surface with the glossiness lower than that of the solder leveler forming surface 16a in the surface of the board 6 as the background surface.

When the upper surface of the board 6 is irradiated with the illumination lights by an illuminating part 25 and the reflected lights of the illumination lights are received from the upper part to pick up the image of the upper surface of the board 6, the upper surface of the board 6 is irradiated with the illumination lights from the light applying direction in which the regularly reflected lights from the solder leveler surface 16a are not received by the camera 23. Specifically, as shown in FIG. 7(b), the upper surface of the board is irradiated with the white illumination lights from a direction in which an illumination angle of θ1 formed by the light applying direction to the solder leveler surface 16a and the surface of the board 6 is 45° or smaller in a vertical plane, and as shown in FIG. 9(c), from a direction in which an angle of θ3 formed by the light applying direction to the solder leveler surface 16a and the boundary of the electrode 16 is 75° or smaller in a horizontal plane.

Further, in the image pick-up, the upper surface of the board 6 is irradiated with the red color illumination lights (colored illumination lights) as well as the white color illumination lights by the red color light source parts 35R of the lower stage illuminating unit 26, the intermediate stage illuminating unit 27 and the upper stage illuminating unit 28 from the light applying direction in which the regularly reflected lights from the solder leveler surface 16a are received by the camera 23. That is, in the image recognition method according to this embodiment, the white color light source parts 35W of the lower stage illuminating unit 26 serve first illuminating means for emitting the white color illumination lights. The red color light source parts 35R of the lower stage illuminating unit 26, the intermediate stage illuminating unit 27 and the upper stage illuminating unit 28 serve as second illuminating means for emitting colored illumination lights.

Thus, the solder leveler surface 16a and the solder surface 9a can be identified in accordance with an obvious color difference between a red color part and a white color part. Even when the cream solder 9 naturally including the same material is printed on the solder leveler surface 16a, a recognition accuracy can be improved to detect a solder area with high accuracy. Further, in this embodiment, since the cream solder 9 can be separated from the solder leveler surface 16a on the same recognition screen, a recognition tact time can be more shortened than a usual recognition method in which a plurality of images picked up under different illuminating conditions need to be obtained.

In the above-described embodiment, the example that the alignment is carried out in such a way that the boundaries of four sides showing the external form of the electrode 16 respectively substantially correspond to the directions of 0°, 90°, 180°, and 270° is described. However, as shown in FIG. 14(a), when the direction of the electrode 16 on the board 6 is inclined by an angle of α from a state shown in FIG. 9(a), a lower illuminating unit 26 is rotated by the same angle of α by a lower stage illumination rotating and driving part 32 (see FIG. 6). Thus, as shown in FIG. 14(b), white illumination lights are applied from the same light applying direction as that of the example shown in FIG. 9(c).

Further, the above-described embodiment shows the example that the board 6 in which the cream solder 9 is printed on the electrode 16 having the solder leveler forming surface 16a serves as the object to be recognized. However, the present invention may be applied to other combinations than the above-described object to be recognized and an object to be recognized including a background surface, a first surface with a glossiness and a second surface with a glossiness lower than that of the first surface in a recognition surface, the first surface being partitioned by a rectangular boundary and the second surface being provided on the first surface in the background surface.

According to the present invention, the object to be recognized is irradiated with the illumination lights by the illuminating part and when the reflected lights of the illumination lights are received from the upper part to pick up the image of the object to be recognized, the object to be recognized is irradiated with the illumination lights from the light applying directions in which the regularly reflected lights from the first surface having the glossiness are not received by the camera. Thus, the first surface can be accurately separated from the second surface having the glossiness lower than that of the first surface.

Further, according to the present invention, the object to be recognized is irradiated with the illumination lights by the illuminating part and when the reflected lights of the illumination lights are received from the upper part to pick up the image of the object to be recognized, the object to be recognized is irradiated with the white illumination lights by the first illuminating unit from the first light applying directions in which the regular reflected lights from the first surface are not received by the camera and the object to be recognized is irradiated with the colored illumination lights by the second illuminating unit from the second light applying directions in which the reflected lights from the first surface are received by the camera. Thus, the first surface and the second surface can be identified on the same recognition screen from the image obtained by one image pick-up operation.

What is claimed is:

1. An image recognition apparatus in which an image obtained by picking up an image of an object to be recognized that includes a background surface, a first surface with a glossiness and a second surface with a glossiness lower than that of the first surface in a recognition surface, the first surface being partitioned by a rectangular boundary and the second surface being provided on the first surface in the background surface, is subjected to a recognition process to discriminate the first surface from the second surface in the background surface, said image recognition apparatus comprising:

an illuminating part for applying illumination light to the object to be recognized upon picking up the image;

a camera for receiving the reflected light of the illumination light from an upper part to pick up the color image of the object to be recognized; and a recognizing process part for recognizing image data obtained by the camera and discriminating the first surface from the second surface based on a luminance difference between the first surface and the second surface in said image, wherein the illuminating part includes a first illuminating unit for applying white illumination light to the object to be recognized from a first light applying direction in which regularly reflected light from the first surface is not received by the camera and a second illuminating unit for applying colored illumination light to the object to be recognized from a second light applying direction in which the reflected light from the first surface is received by the camera, wherein an angle, that occurs in a vertical plane, and that is formed by the first light applying direction with both of the first surface and the background surface, is not greater than 45 degrees, and an angle, that occurs in a horizontal plane, and that is formed by the first light applying direction and the boundary, is not greater than 75 degrees, and wherein an angle, that occurs in a vertical plane, and that is formed by the second light applying direction with both of the first surface and the background surface, is not greater than 45 degrees.

2. An image recognition apparatus according to claim 1, wherein the object to be recognized is a board for mounting electronic parts after a solder printing, the background surface shows the surface of the board, the first surface shows an electrode for connecting the electronic parts provided on the board and having a solder leveler formed on its surface and the second surface shows a cream solder printed on the electrode.

3. An image recognition apparatus according to claim 2, wherein, the image is picked up after the cream solder is printed on the electrode and before an electronic part is mounted on the electrode.

4. An image recognition method in which an image obtained by picking up an image of an object to be recognized that includes a background surface, a first surface with a glossiness and a second surface with a glossiness lower than that of the first surface in a recognition surface, the first surface being partitioned by a rectangular boundary and the second surface being provided on the first surface in the background surface, is subjected to a recognition process to discriminate the first surface from the second surface in the background surface, said image recognition method comprising the steps of:

irradiating the object to be recognized with white illumination light by a first illuminating unit from a first light applying direction in which regularly reflected light from the first surface is not received by a camera when the object to be recognized is irradiated with the illumination light by an illuminating part and the reflected light of the illumination light is received from an upper part to pick up the image of the object to be recognized, wherein an angle, that occurs in a vertical plane, and that is formed by the first light applying direction with both of the first surface and the background surface, is not greater than 45 degrees, and an angle, that occurs in a horizontal plane, and that is formed by the first light applying direction and the boundary, is not greater than 75 degrees; and irradiating the object to be recognized with colored illumination light by a second illumination unit from a second light applying direction in which the reflected light from the first surface is received by the camera, wherein an angle, that occurs in a vertical plane, and that is formed by the second light applying direction with both of the first surface and the background surface, is not greater than 45 degrees; and discriminating the first surface from the second surface based on a luminance difference between the first surface and the second surface in said image.

5. An image recognition method according to claim 4, wherein the background surface shows a board for mounting electronic parts, the first surface shows an electrode for connecting the electronic parts provided on the board and having a solder leveler formed on its surface and the second surface shows a cream solder printed on the electrode.

6. An image recognition method according to claim 5, wherein the image is picked up after the cream solder is printed on the electrode and before an electronic part is mounted on the electrode.

* * * * *

UNITED STATES PATENT AND TRADEMARK OFFICE
CERTIFICATE OF CORRECTION

PATENT NO. : 7,551,768 B2  Page 1 of 1
APPLICATION NO. : 10/753740
DATED : June 23, 2009
INVENTOR(S) : Yasuichi Okada, Kimiyuki Yamasaki and Masahiro Kihara It is certified that error appears in the above-identified patent and that said Letters Patent is hereby corrected as shown below:

In Column 1, line 9, please delete "2001-003032" and insert therefore --2003-003032--.

In Column 13, line 38, please delete:
"3. An image recognition apparatus according to claim 2, wherein the image is picked up after the cream solder is printed on the electrode and before an electronic part is mounted on the electrode.".

In Column 14, line 45, please insert therefore --7. An image recognition apparatus according to claim 2, wherein the image is picked up after the cream solder is printed on the electrode and before an electronic part is mounted on the electrode.--.

Signed and Sealed this

First Day of September, 2009

David J. Kappos
*Director of the United States Patent and Trademark Office*